US010627398B2

(12) United States Patent
Ono et al.

(10) Patent No.: US 10,627,398 B2
(45) Date of Patent: Apr. 21, 2020

(54) ANALYSIS DEVICE AND ANALYSIS METHOD

(71) Applicant: JVC KENWOOD Corporation, Yokohama-shi, Kanagawa (JP)

(72) Inventors: Masayuki Ono, Yokohama (JP); Shingo Yagyu, Yokohama (JP); Makoto Itonaga, Yokohama (JP); Yuichi Hasegawa, Yokohama (JP); Koji Tsujita, Yokohama (JP)

(73) Assignee: JVC KENWOOD CORPORATION, Yokohama-Shi, Kanagawa (JP)

( * ) Notice: Subject to any disclaimer, the term of this patent is extended or adjusted under 35 U.S.C. 154(b) by 0 days.

(21) Appl. No.: 16/412,807

(22) Filed: May 15, 2019

(65) Prior Publication Data
US 2019/0265237 A1    Aug. 29, 2019

Related U.S. Application Data

(60) Division of application No. 15/271,328, filed on Sep. 21, 2016, now abandoned, which is a continuation of
(Continued)

(30) Foreign Application Priority Data

Mar. 31, 2014 (JP) .................................. 2014-072536

(51) Int. Cl.
*G01N 15/14* (2006.01)
*G01N 33/543* (2006.01)
(Continued)

(52) U.S. Cl.
CPC ... *G01N 33/54366* (2013.01); *G01N 15/0612* (2013.01); *G01N 15/1429* (2013.01);
(Continued)

(58) Field of Classification Search
CPC ........... G01N 15/0205; G01N 15/1429; G01N 15/1459; G01N 2015/0238;
(Continued)

(56) References Cited

U.S. PATENT DOCUMENTS 4,412,175 A * 10/1983 Maynarez .......... G01N 15/1227
324/71.1
4,491,926 A * 1/1985 Okada ................ G01N 15/1227
324/71.4
(Continued)

FOREIGN PATENT DOCUMENTS

JP          5-5741 A     1/1993
JP     2002-530786 A    9/2002

OTHER PUBLICATIONS

Supplementary European Search Report dated Mar. 17, 2017 corresponding to application No. 15772829.6-1553.
(Continued)

*Primary Examiner* — Hoa Q Pham
(74) *Attorney, Agent, or Firm* — Nath, Goldberg & Meyer; Jerald L. Meyer

(57) ABSTRACT

An analysis device optically scans a surface of a substrate to which particles are fixed, detects a pulse wave included in a detection signal obtained from an optical scanning unit when the optical scanning unit scans the substrate, and counts the particles based on pulse interval between two pulse waves each having pulse width less than first reference value determined depending on first pulse width when the optical scanning unit scans a plurality of particles adjacent to each other when the two pulse waves are detected consecutively.

5 Claims, 9 Drawing Sheets

Related U.S. Application Data application No. PCT/JP2015/057303, filed on Mar. 12, 2015.

(51) Int. Cl.
*G01N 15/06* (2006.01)
*G01N 15/00* (2006.01)

(52) U.S. Cl.
CPC ..... *G01N 15/1434* (2013.01); *G01N 15/1456* (2013.01); *G01N 33/543* (2013.01); *G01N 2015/0038* (2013.01); *G01N 2015/0065* (2013.01); *G01N 2015/1486* (2013.01)

(58) Field of Classification Search
CPC ....... G01N 2015/1486; G01N 15/0211; G01N 2021/4716
USPC ............................ 356/335–343, 73
See application file for complete search history.

(56) References Cited

U.S. PATENT DOCUMENTS

| | | | | |
|---|---|---|---|---|
| 5,059,395 A | * | 10/1991 | Brittenham | G01N 15/1456 356/335 |
| 5,172,004 A | | 12/1992 | Furuya | |
| 5,561,515 A | * | 10/1996 | Hairston | G01P 5/22 356/28 |
| 6,573,696 B1 | * | 6/2003 | Sahner | G01N 15/1429 324/601 |
| 6,829,208 B1 | | 12/2004 | Furumiya | |
| 7,688,427 B2 | | 3/2010 | Cox | |
| 9,140,638 B2 | * | 9/2015 | Pariseau | G01N 15/0205 |
| 2006/0044558 A1 | * | 3/2006 | Furukawa | G01N 21/51 356/338 |
| 2008/0068952 A1 | | 3/2008 | Yamada | |
| 2008/0221812 A1 | * | 9/2008 | Pittaro | G01N 15/14 702/66 |
| 2010/0035235 A1 | | 2/2010 | Gabriel | |
| 2012/0288408 A1 | | 11/2012 | Ono et al. | |
| 2013/0122488 A1 | | 5/2013 | Tanabe et al. | |

OTHER PUBLICATIONS

K. Tsujita, et al., "Ultrahigh-Sesitivity Biomarker Sensing system Based on the Combination of Optical Disc Technologies and Nanobead Technologies", Japanese Journal of Applied Physics 52 92018) 09LB02.

Written Opinion Form PCT/ISA/237 issued in corresponding international application No. PCT/JP2015/057303 dated Jun. 9, 2015.

International Search Report issued in corresponding international application No. PCT/JP2015/057303 dated Jun. 9, 2015.

Encyclopedia of Database Systems, Thijs Westerveld, 2009 Edition (https://doi.org/10.1007/978-0-387-39940-9_213) (Year 2009).

* cited by examiner

ANALYSIS DEVICE AND ANALYSIS METHOD

CROSS REFERENCE TO RELATED APPLICATION

This is a Divisional Application of U.S. patent application Ser. No. 15/271,328, filed Sep. 21, 2016, an application filed as Continuation of Application No. PCT/JP2015/057303 filed Mar. 12, 2015 and claiming benefit from Japanese Application No. 2014-072536, filed Mar. 31, 2014, the content of each of which is hereby incorporated by reference in its entirety.

BACKGROUND

The present disclosure relates to an analysis device and an analysis method for analyzing biomaterials such as antibodies and antigens.

Immunoassays are known that quantitatively analyze disease detection and therapeutic effects by detecting particular antigens or antibodies as biomarkers associated with diseases. One of the immunoassays is an enzyme-linked immunosorbent assay (ELISA) for detecting antigens or antibodies labeled by enzymes, which is widely used because of having the advantage of low costs. The ELISA requires a long period of time, such as from several hours to a day, to complete a series of multiple steps including pretreatment, antigen-antibody reaction, bond/free (B/F) separation, and enzyme reaction.

Another technology is disclosed in which antibodies fixed to an optical disc are allowed to bind to antigens in a specimen, and the antigens are further bound to particles having antibodies and then scanned with an optical head, so as to count the particles captured on the disc in a short period of time (Japanese Unexamined Patent Application Publication No. H05-005741). Still another technology is disclosed in which biosamples or particles are adsorbed to a surface of an optical disc on which a tracking structure is formed, so as to detect changes in signal by an optical pickup (Japanese Translation of PCT International Application Publication No. 2002-530786).

SUMMARY

The technology disclosed in Japanese Unexamined Patent Application Publication No. H05-005741 or Japanese Translation of PCT International Application Publication No. 2002-530786, however, may fail to obtain detection signals corresponding to particles depending on the type and arrangement of the particles used. Such failure leads to inaccurate counting results, which may decrease the performance of quantitative analysis of analytes.

A first aspect of the present embodiment provides an analysis device including: an optical scanning unit configured to optically scan a surface of a substrate to which particles are fixed; a pulse detector configured to detect a pulse wave and a pulse width of the pulse wave included in a detection signal obtained from the optical scanning unit when the optical scanning unit scans the substrate; and a counting unit configured to count the particles based on a pulse interval between two pulse waves each having a pulse width less than a first reference value when the pulse detector consecutively detects the two pulse waves.

A second aspect of the present embodiment provides an analysis method including: optically scanning a surface of a substrate to which particles are fixed; detecting a pulse wave and a pulse width of the pulse wave included in a detection signal obtained by scanning the substrate; and counting the particles based on a pulse interval between two pulse waves each having a pulse width less than a first reference value when the two pulse waves are consecutively detected in the detection signal.

DETAILED DESCRIPTION

Figure 1:
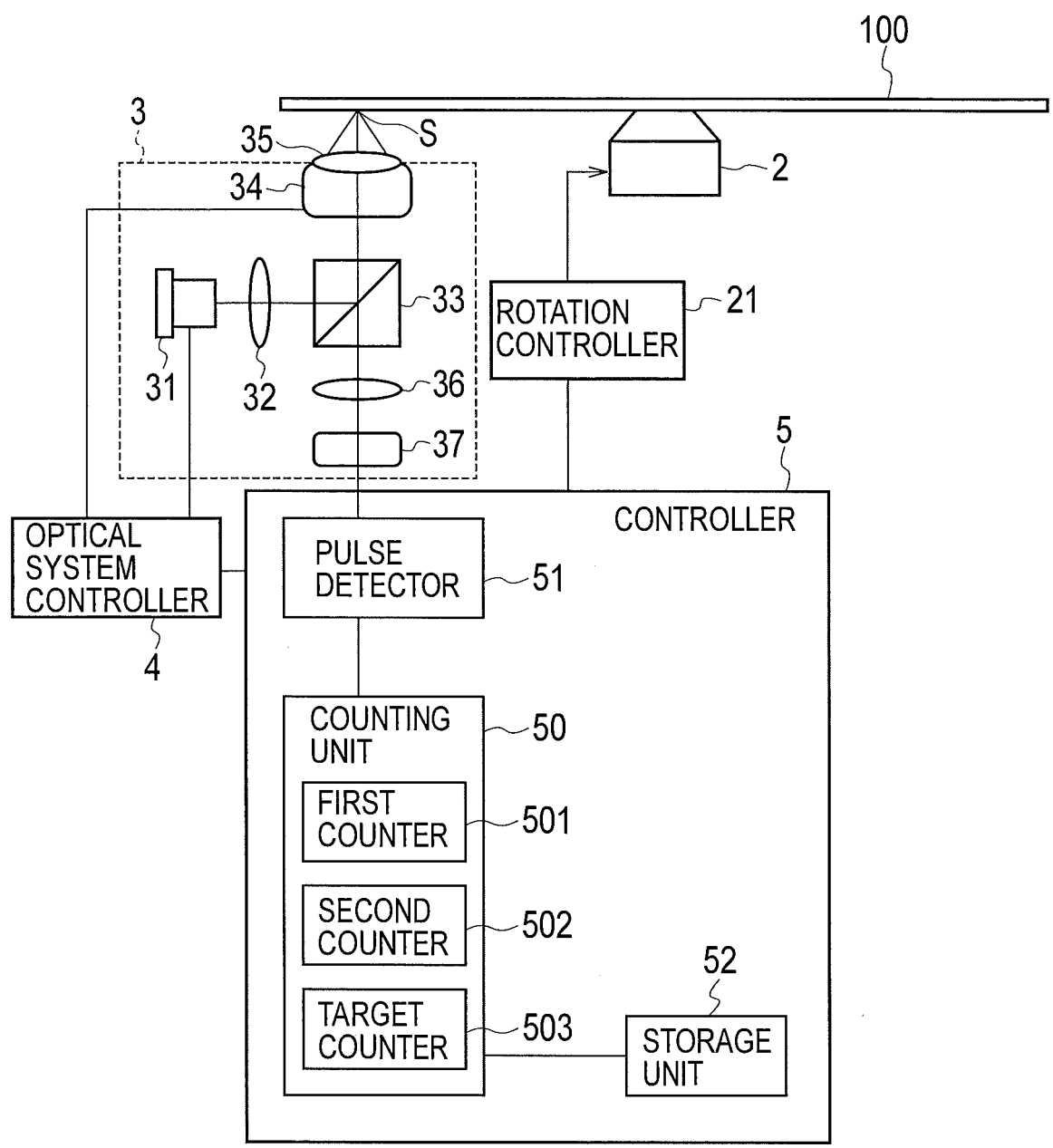
FIG. 1 is a schematic block diagram for describing a fundamental configuration of an analysis device according to an embodiment.

Hereinafter, an embodiment will be described with reference to the drawings. The same or similar elements shown in the drawings are designated by the same or similar reference numerals below, and overlapping descriptions thereof are not repeated herein.

[Analysis Device]

As shown in FIG. 1, an analysis device according to the embodiment includes a substrate 100, a motor 2 that rotates the substrate 100, an optical scanning unit 3 that optically scans the substrate 100, and a controller 5 that controls the motor 2 and the optical scanning unit 3.

The substrate 100 is formed into a circular shape having substantially the same dimensions as optical discs such as compact discs (CDs), digital versatile discs (DVDs), and Blu-ray discs (BD). The substrate 100 has a track structure on the surface thereof that the optical scanning unit 3 can scan. The track structure includes, for example, grooves, lands, and pits, and is formed into a spiral extending from the inner side to the outer side. The substrate 100 is formed of a hydrophobic resin material, such as polycarbonate resin and cycloolefin polymer, used for common optical discs. The substrate 100 may be, as necessary, provided with a thin film on the surface thereof, or subjected to surface treatment with a silane coupling agent.

Figure 2A:
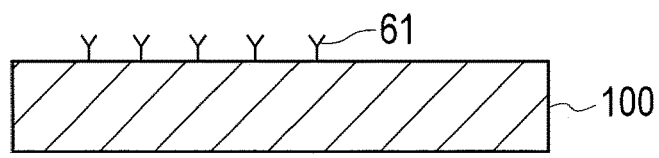
FIG. 2A to FIG. 2F are enlarged cross-sectional views each schematically showing a substrate of the analysis device according to the embodiment, for describing an example of a method of fixing antibodies, antigens, and beads to the substrate.

As shown in FIG. 2A, antibodies 61 specifically binding to antigens 62, which are biomaterials serving as analytes, are fixed to the surface of the substrate 100. The antigens 62 are labeled with beads (particles) 66 to which antibodies 65 specifically binding to the antigens 62 are adsorbed, so that the antigens 62 and the beads 66 are correlatively fixed to the surface of the substrate 100. The antigens 62 are specifically bound to the antibodies 61 and 65, so as to be used as biomarkers serving as indicators of diseases.

Figure 2B:
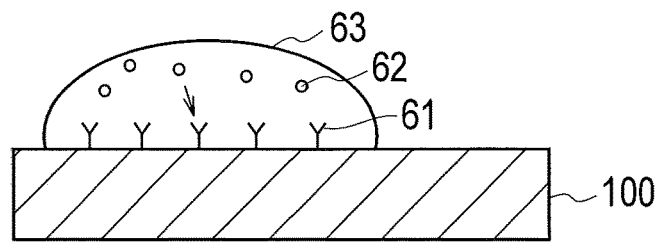
Figure 2C:
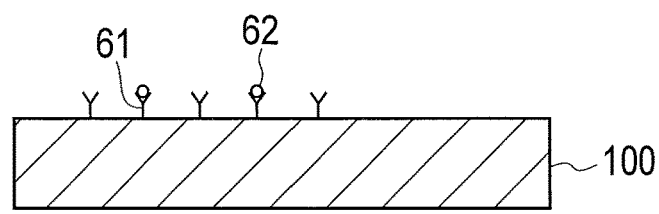

As shown in FIG. 2A, the antibodies 61 are preliminarily fixed to the surface of the substrate 100. The antibodies 61 are bound to the surface of the substrate 100 due to hydrophobic binding or covalent binding. The antibodies 61 may be fixed to the surface of the substrate 100 via a substance such as avidin. Then, as shown in FIG. 2B, a sample solution 63 including the antigens 62 is applied dropwise to the surface of the substrate 100. The antigens 62 move through the sample solution 63 by Brownian motion and come into contact with the antibodies 61, so as to be specifically bound to the antibodies 61 by an antigen-antibody reaction. As shown in FIG. 2C, the surface of the substrate 100 to which the sample solution 63 is applied dropwise is subjected to spin washing with pure water or the like, so as to remove the sample solution 63 including excessive antigens 62 not bound to the antibodies 61 from the surface of the substrate 100.

Figure 2D:
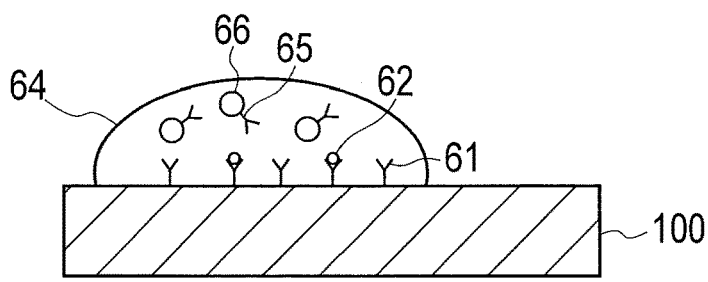

As shown in FIG. 2D, a buffer solution 64 including the beads 66 is applied dropwise to the surface of the substrate 100. The buffer solution 64 may be applied while the sample solution 63 remains on the surface of the substrate 100. The antibodies 65 adsorbed to the beads 66 specifically bind to the antigens 62 by the antigen-antibody reaction. The beads 66 are then bound to the antigens 62, so as to label the antigens 62.

The beads 66 are formed of synthetic resin such as polystyrene including a magnetic material such as ferrite, and formed into a substantially spherical shape. A diameter of the beads 66 is in the range of from several tens of nanometers to several hundreds of nanometers, and a particular example of the diameter is 200 nm. When the buffer solution 64 is applied dropwise, the beads 66 are quickly collected to the surface of the substrate 100 such that a magnet is placed on the opposite side of the surface of the substrate 100, so as to promote the reaction with the antigens 62. In addition, the time required to label the antigens 62 fixed to the substrate 100 can be reduced to approximately several minutes such that the antigens 62 and the beads 66 are simultaneously applied to the substrate 100.

The antibodies 61 and 65 may be any biomaterials having specificity that specifically bind to the antigens 62. A combination of the antibodies 61 and 65 is selected such that the antibodies 61 and 65 separately bind to different sites. For example, when membrane vesicles such as exosomes on which several types of antigens 62 are expressed are used as analytes, the types of the antibodies 61 and 65 are chosen differently from each other, so as to detect a biosample including two types of antigens 62. The antibodies 61 and 65 are, however, not limited thereto, and may be the same type because exosomes, which are different from typical antigens, include multiple antigens of the same kind of protein on the surface thereof.

Figure 2E:
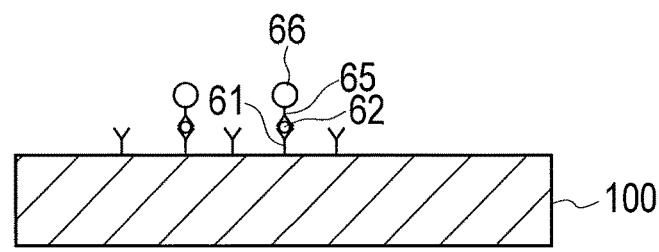
Figure 2F:
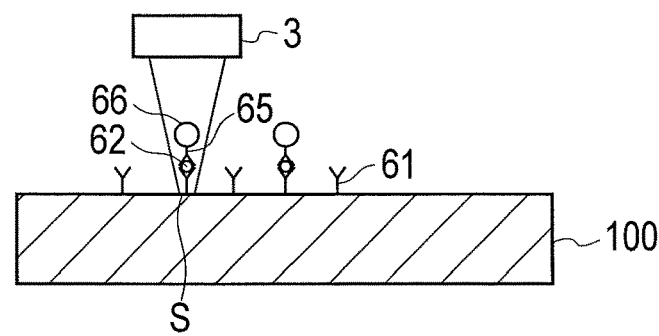

As shown in FIG. 2E, the substrate 100 to which the buffer solution 64 is applied dropwise is washed with, for example, pure water, so as to remove the buffer solution 64 including excessive beads 66 not bound to the antigens 62 from the substrate 100. As shown in FIG. 2F, the substrate 100 is optically scanned by the optical scanning unit 3, so as to detect the beads 66 to analyze the antigens 62 labeled with the beads 66.

As shown in FIG. 1, the optical scanning unit 3 includes a laser oscillator 31, a collimator lens 32, a beam splitter 33, an actuator 34, an objective lens 35, a condensing lens 36, and a light detector 37. The optical scanning unit 3 is an optical pickup that optically scans the substrate 100.

The laser oscillator 31 emits laser light to the collimator lens 32 according to the control by the controller 5. The laser oscillator 31 is a semiconductor laser oscillator that emits laser light having, for example, a wavelength of 405 nm which is the same as that for reproduction of BD, and output of about 1 mW. The collimator lens 32 collimates the laser light emitted from the laser oscillator 31. The beam splitter 33 reflects the laser light collimated by the collimator lens 32 toward the objective lens 35.

The objective lens 35 concentrates the laser light transmitted via the beam splitter 33 on the surface of the substrate 100, to which the antibodies 61 are fixed, due to the operation of the actuator 34 according to the control by the controller 5, so as to image spot S. The objective lens 35 has a numerical aperture of, for example, 0.85. The laser light concentrated by the objective lens 35 is reflected from the substrate 100 and then reaches the beam splitter 33. The incident laser light passes through the beam splitter 33 and further reaches the light detector 37 via the condensing lens 36. The condensing lens 36 concentrates the laser light reflected from the substrate 100 into the light detector 37. The light detector 37 is, for example, a photodiode to output, to the controller 5, a detection signal corresponding to the volume of the laser light reflected from the substrate 100.

The controller 5 controls the operation of the motor 2 via a rotation controller 21. The motor 2 is controlled by the controller 5 to rotate the substrate 100 at a constant linear velocity (CLV). The linear velocity is, for example, 4.92 m/s.

The controller 5 controls the operation of the laser oscillator 31 and the actuator 34 via an optical system controller 4. The actuator 34 is controlled by the controller 5 to move the optical scanning unit 3 in a radial direction of the substrate 100 so as to spirally scan the surface of the rotating substrate 100. The controller 5 also detects errors such as focus errors (FE) or tracking errors (TE) from the detection signal output from the light detector 37. The controller 5 controls the actuator 34 and other components to appropriately scan the surface of the substrate 100 depending on the errors detected.

The controller 5 includes a pulse detector 51, a storage unit 52, and a counting unit 50. The pulse detector 51 inputs the detection signal output from the light detector 37. The pulse detector 51 detects a pulse wave and a pulse width of the pulse wave included in the detection signal obtained from the optical scanning unit 3. The pulse detector 51 is a signal processing device such as a digital signal processor (DSP). The storage unit 52 is a memory such as a semiconductor memory. The storage unit 52 stores reference values corresponding to the pulse wave and the pulse width detected by the pulse detector 51.

The counting unit 50 counts the number of beads 66 fixed to the surface of the substrate 100 according to the pulse wave detected by the pulse detector 51 and the reference values stored in the storage unit 52. The counting unit 50 is, for example, a central processing unit (CPU). The counting unit 50 includes, as a logical structure, a first counter 501, a second counter 502, and a target counter 503.

The first counter 501 measures pulse width Ta of the pulse wave detected by the pulse detector 51. The second counter 502 measures, depending on the pulse width Ta of the pulse wave detected by the pulse detector 51, pulse interval Tb between the pulse wave and a pulse wave subsequently detected. The target counter 503 counts the number of beads 66 according to the measurement results by the first counter 501 and the second counter 502 and the reference values stored in the storage unit 52.

—Reference Values—

Figure 3:
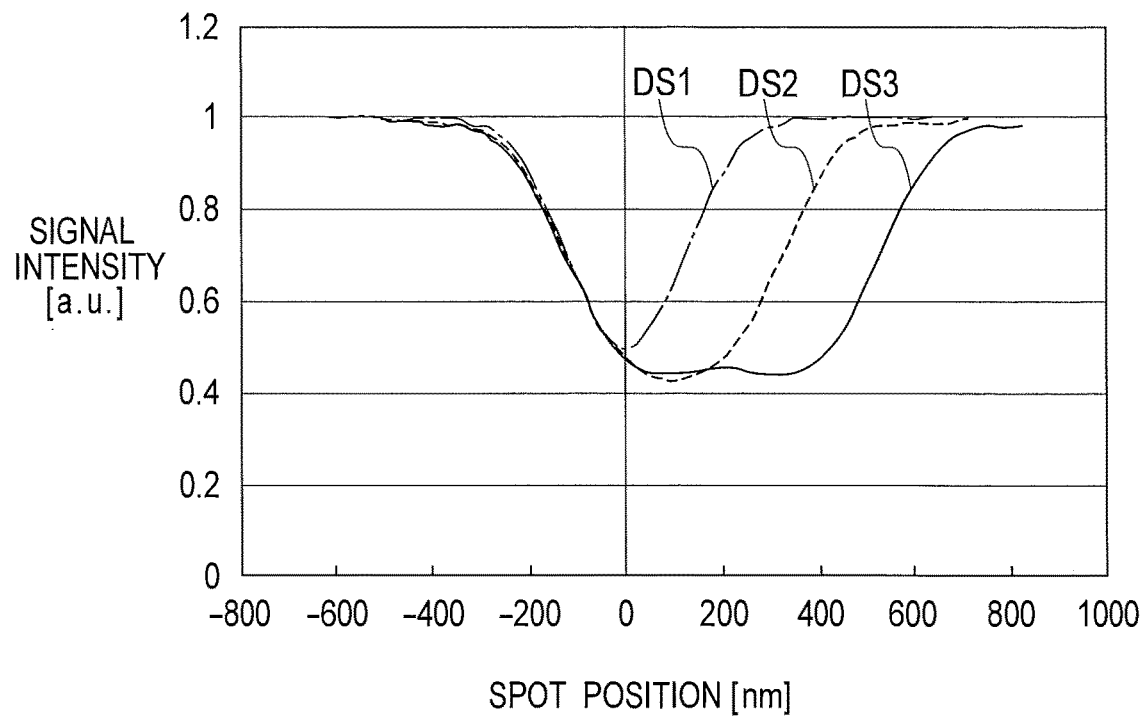
FIG. 3 is a view showing simulation results of detection of adjacent beads while varying the number of beads, for describing characteristics between a spot position and signal intensity when scanning the substrate.

FIG. 3 shows simulation results of three detection signals DS1 to DS3 obtained in such a manner as to scan each of one projection pit assuming that one bead is present on the substrate 100, adjacent two projection pits assuming that two beads are present on the substrate 100, and adjacent three projection pits assuming that three beads are present on the substrate 100. The transverse axis represents a position of the spot S corresponding to each front bead 66 in a particular interval, and the vertical axis represents signal intensity obtained such that each signal is normalized by a detection signal detected when there is no bead 66. The pulse width is assumed to gradually increase as the number of beads 66 increases, as indicated by the detection signal DS1 with one isolated bead 66, the detection signal DS2 with two beads 66, and the detection signal DS3 with three beads 66 in this order.

Figure 4:
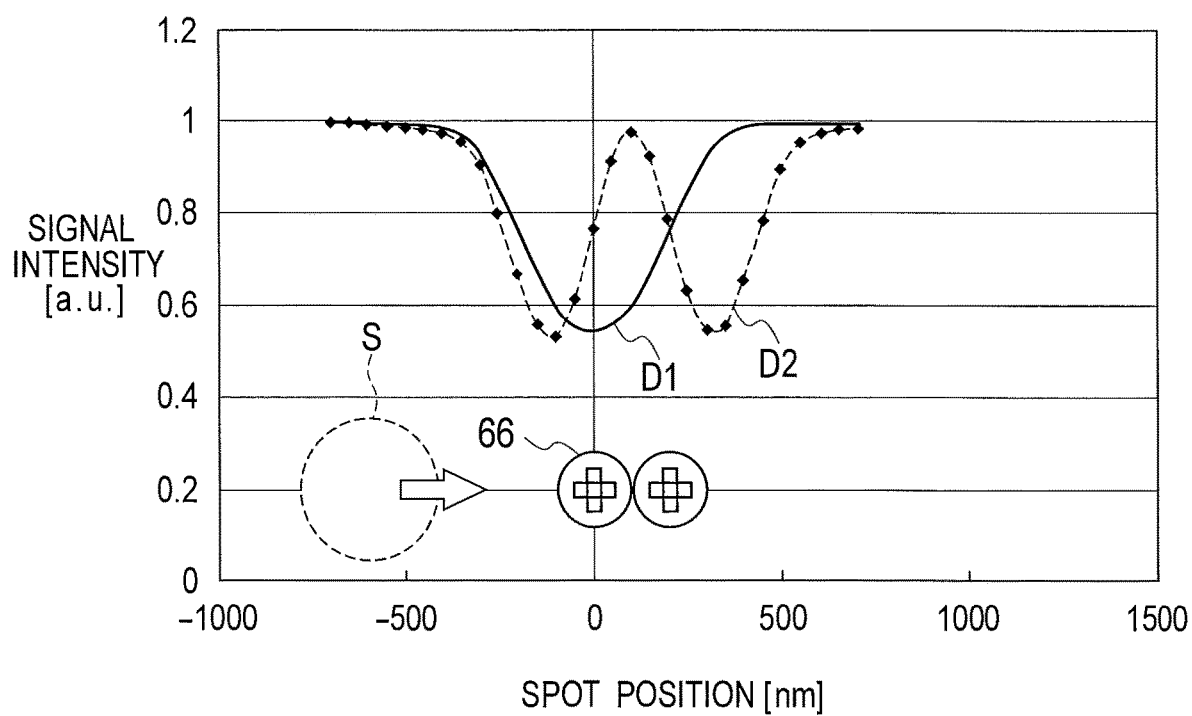
FIG. 4 is a view for describing characteristics between a spot position and signal intensity when scanning the substrate of the analysis device according to the embodiment, in which adjacent beads are detected while varying the number of beads.
Figure 5:
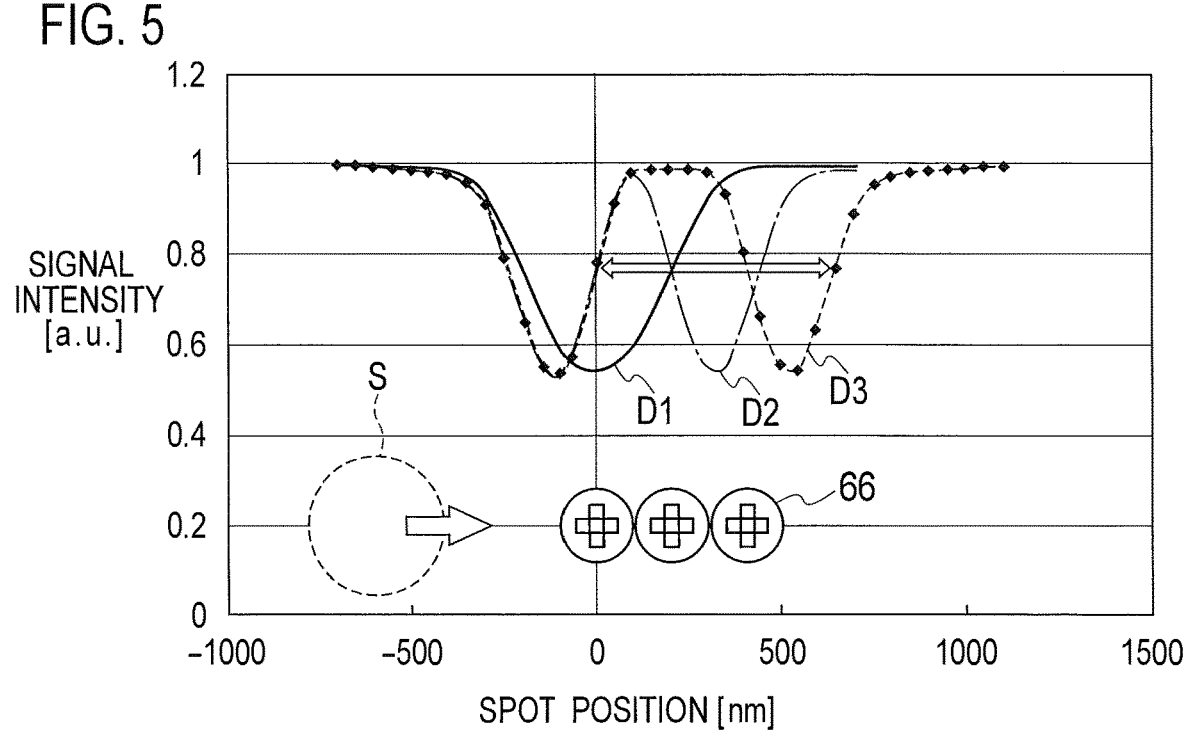
FIG. 5 is a view for describing characteristics between a spot position and signal intensity when scanning the substrate of the analysis device according to the embodiment, in which adjacent beads are detected while varying the number of beads.

As shown in FIG. 4, however, a detection signal D2 obtained such that adjacent two beads 66 are actually scanned includes two pulse waves with substantially the same pulse width which is smaller than a pulse width of a detection signal D1 obtained such that one isolated bead 66 is scanned. As shown in FIG. 5, a detection signal D3 obtained such that adjacent three beads are actually scanned includes two pulse waves having substantially the same pulse width as those of the detection signal D2 and having a larger pulse interval than the detection signal D2. A detection signal with adjacent four beads 66 scanned also includes two pulse waves having substantially the same width as those of the detection signal D2 and having a larger pulse interval than the detection signal D3.

When the diameter of beads 66 is approximately one half of the wavelength of the laser light scanned, and there are a plurality of beads 66 adjacent to each other, the number of beads cannot be counted accurately, which may decrease the performance of quantitative analysis of the analytes. The inventors resolved the effects of light on a structure (particles) with a smaller size than a wavelength of the light having different pits from common optical discs as described above, by solving Maxwell's equations with regard to times and space variables by a finite-difference time-domain (FDTD) method. The counting unit 50 can count the number of beads 66 with high accuracy when a plurality of beads 66 adjacent to each other are present on the substrate 100, on the basis of the predetermined reference values stored in the storage unit 52.

Figure 6:
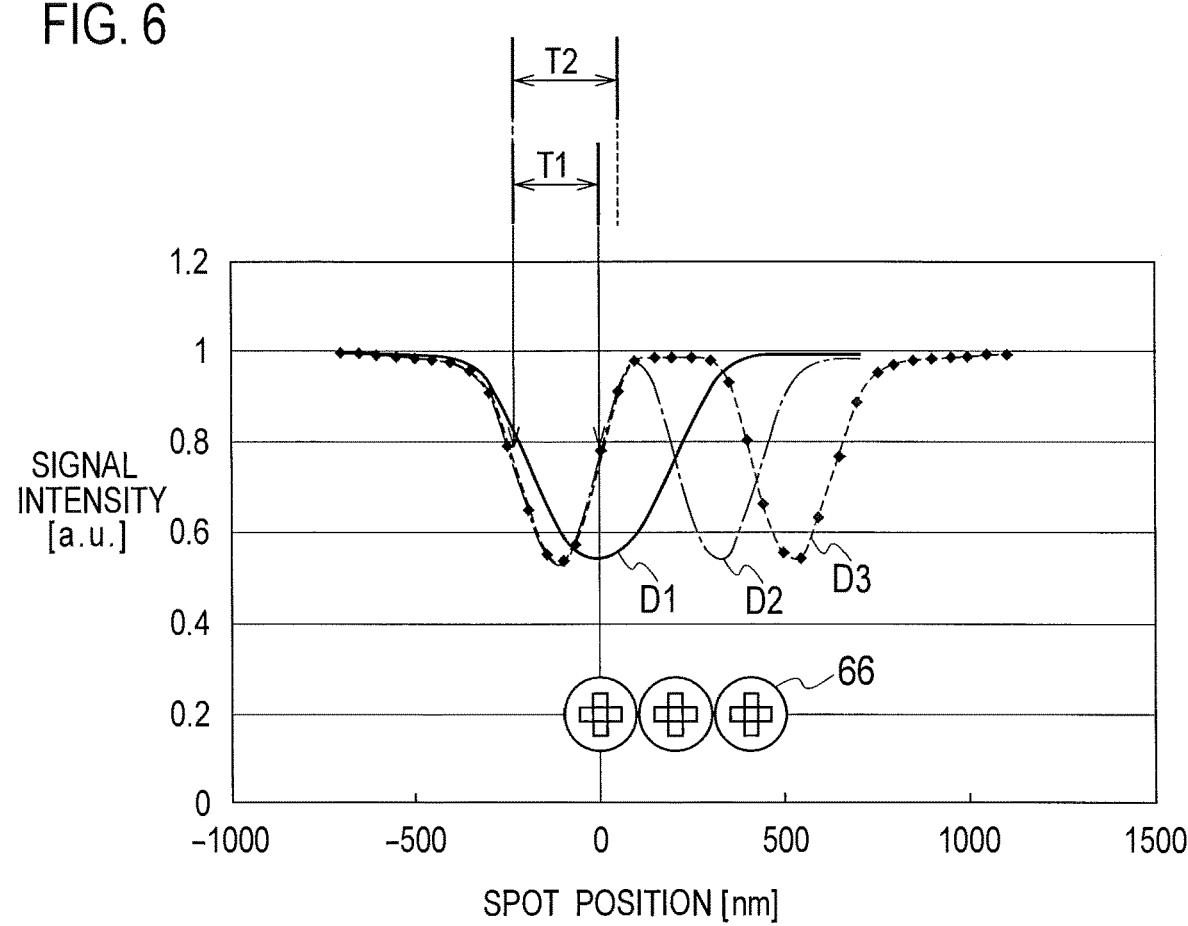
FIG. 6 is a view for describing a method of determining a reference value stored in a storage unit included in the analysis device according to the embodiment.

As shown in FIG. 6, the storage unit 52 preliminarily stores first pulse width T1 of the respective detection signals D2 and D3 and first reference value T2 determined depending on the first pulse width T1 when the optical scanning unit 3 scans a plurality of beads 66 adjacent to each other. The first reference value T2 is, for example, the sum of the first pulse width T1 and a predetermined value. The predetermined value added to the first pulse width T1 may be a jitter value included in the detection signal. The predetermined value added to the first pulse width T1 may also be approximately 100% to 130% of the jitter value. The first reference value T2 may be a predetermined percentage of the first pulse width T1. For example, the first reference value T2 is approximately 100% to 130% of the first pulse width T1.

Figure 7:
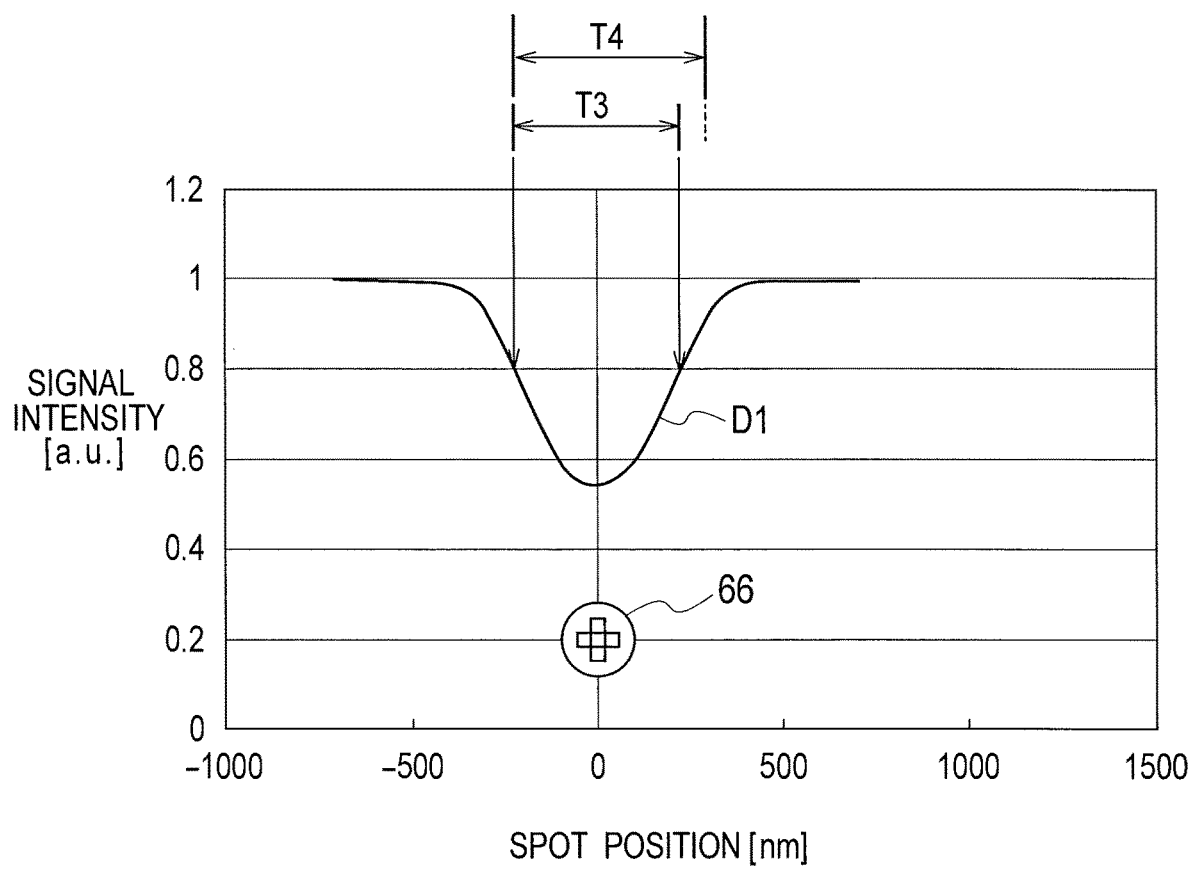
FIG. 7 is a view for describing a method of determining a reference value stored in the storage unit included in the analysis device according to the embodiment.

As shown in FIG. 7, the storage unit 52 preliminarily stores second pulse width T3 of the detection signal D1 and second reference value T4 determined depending on the second pulse width T3 when the optical scanning unit 3 scans a bead 66 isolated from other beads 66. The second reference value T4 is, for example, the sum of the second pulse width T3 and a predetermined value. The predetermined value added to the second pulse width T3 may be a jitter value included in the detection signal. The predetermined value added to the second pulse width T3 may also be approximately 100% to 130% of the jitter value. The second reference value T4 may be a predetermined percentage of the second pulse width T3. For example, the second reference value T4 is approximately 100% to 130% of the second pulse width T3.

<Analysis Method>

Figure 8:
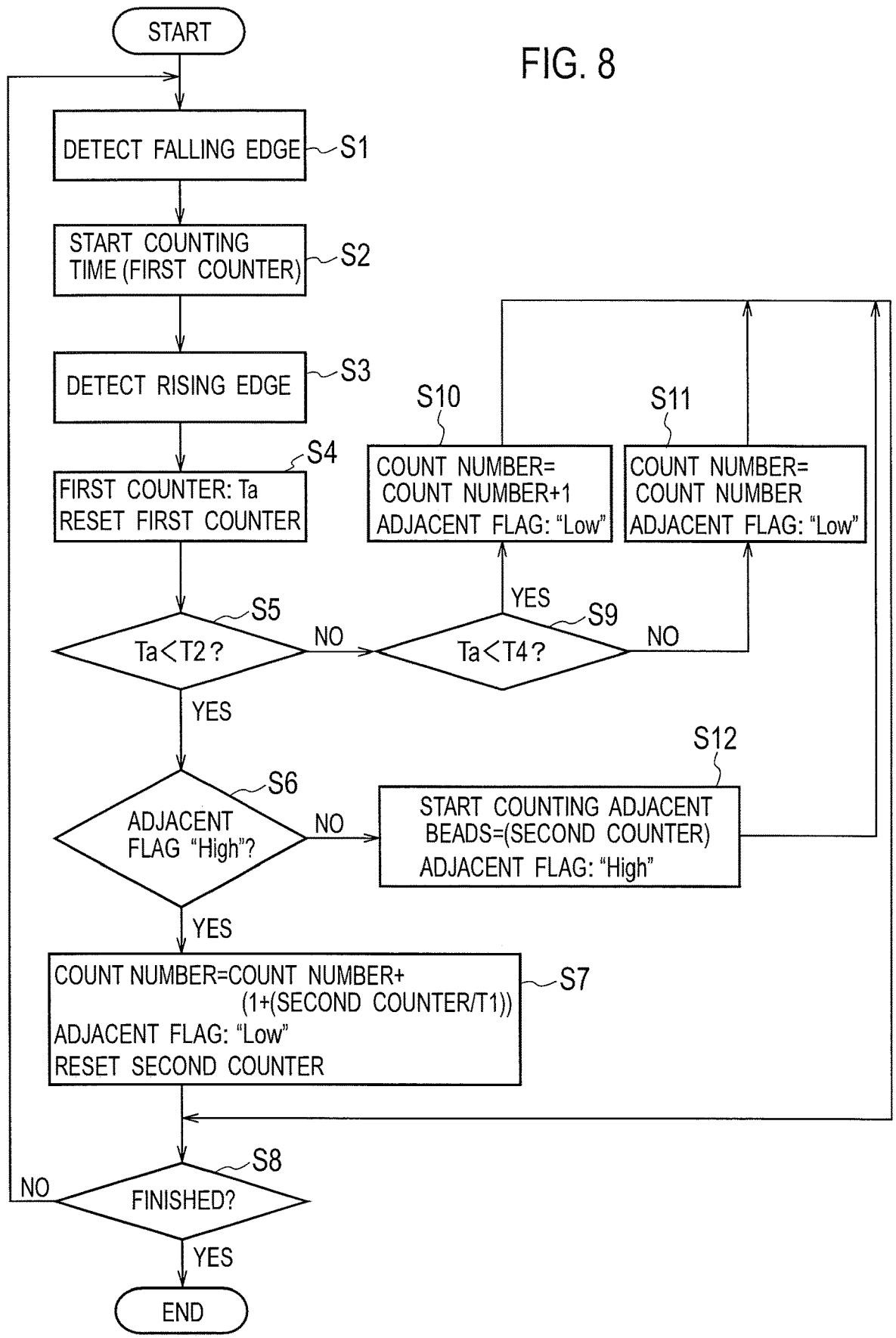
FIG. 8 is a flowchart for describing the operation of the analysis device according to the embodiment.

An analysis method by the analysis device according to the embodiment is described below with reference to the flowchart shown in FIG. 8, in which the optical scanning unit 3 optically scans the substrate 100, and the counting unit 50 counts the number of beads 66 fixed to the substrate 100, so as to analyze the analytes labeled by the beads 66.

First, the operator allows the rotation controller 21 and the optical system controller 4 to respectively start operations of the motor 2 and the optical scanning unit 3 according to the control by the controller 5. The substrate 100 to which antigens 62 and beads 66 are fixed on the surface thereof by the antigen-antibody reaction, is rotated at a constant linear velocity by the motor 2, so as to be optically scanned by the optical scanning unit 3. The optical scanning unit 3 detects, with the light detector 37, the laser light emitted from the laser oscillator 31 and reflected from the surface of the substrate 100. The light detector 37 outputs a detection signal corresponding to the volume of the detected laser light to the pulse detector 51.

In step S1, the pulse detector 51 obtains the detection signal output from the light detector 37 to detect a falling edge of the obtained detection signal. The pulse detector 51 preliminarily holds a threshold set to intensity corresponding to approximately one half of a peak value of the detection signal detected when beads 66 are scanned, and detects a point where the detection signal falls below the threshold as a falling edge of the detection signal.

Figure 9:
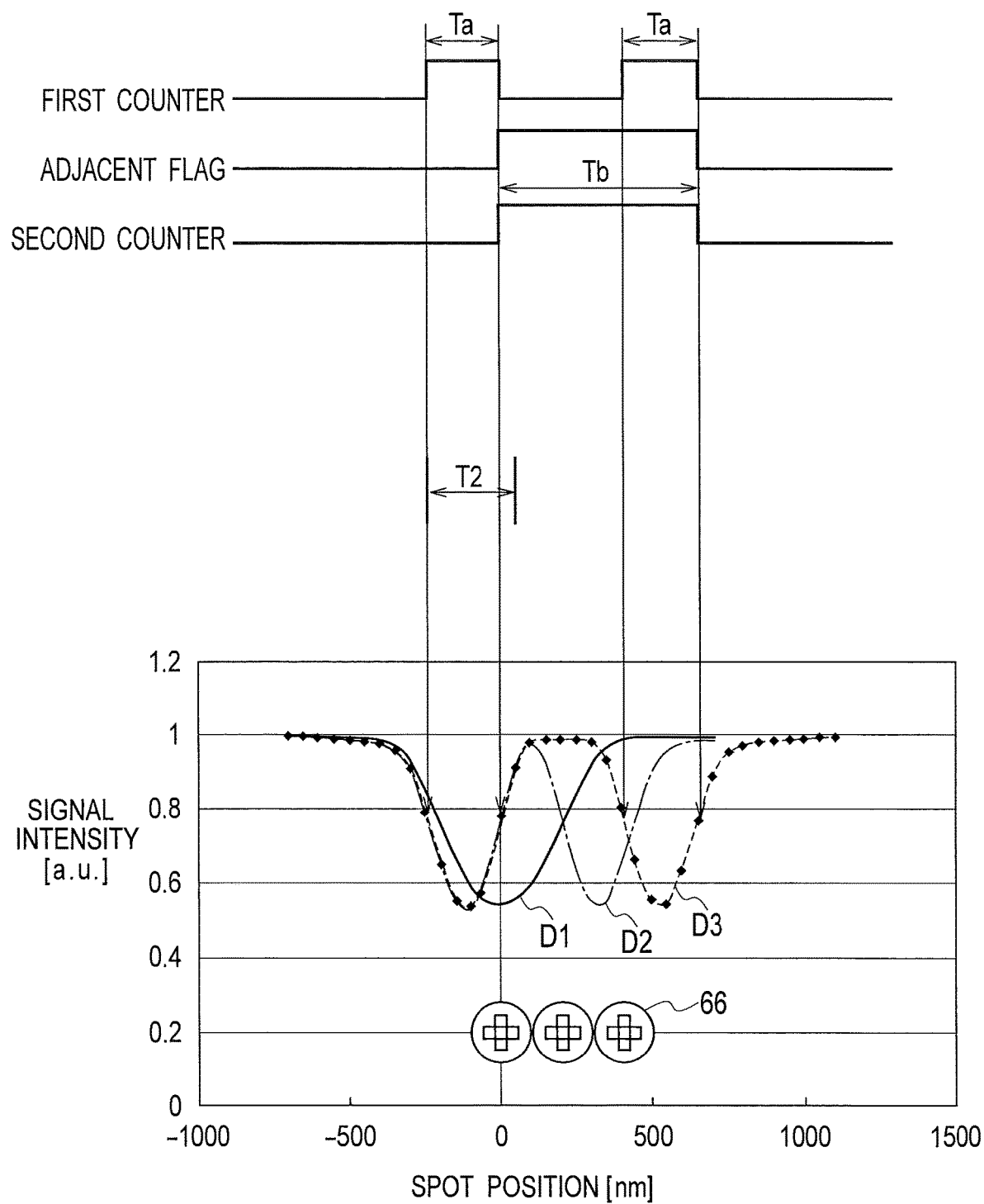
FIG. 9 is a view for describing the operation of the analysis device according to the embodiment.

In step S2, the first counter 501 starts measuring time Ta from the point where the falling edge is detected in step S1, as shown in FIG. 9.

In step S3, the pulse detector 51 detects a rising edge of the detection signal obtained from the light detector 37. The pulse detector 51 preliminarily holds the threshold set to the intensity corresponding to approximately one half of the peak value of the detection signal detected when beads 66 are scanned, and detects a point where the detection signal exceeds the threshold as a rising edge of the detection signal.

In step S4, the first counter 501 fixes the time Ta from the point where the falling edge is detected in step S1 to the point where the rising edge is detected in step S3, and resets it. The target counter 503 obtains and holds the time Ta fixed by the first counter 501 as a pulse width (half width) Ta of the pulse wave detected in steps S1 to S3.

In step S5, the target counter 503 reads out the first reference value T2 from the storage unit 52, and determines whether the pulse width Ta held in step S4 is less than the first reference value T2. The target counter 503 sets the process proceeding to step S6 when the pulse width Ta is less than the first reference value T2, or sets the process proceeding to step S9 when the pulse width Ta is greater than or equal to the first reference value T2.

When the pulse width Ta is less than the first reference value T2 in step S5, the target counter 503 determines whether an adjacent flag is "High" (=1) in step S6. The adjacent flag is a flag set in the target counter 503 in association with the second counter 502. The target counter 503 sets the process proceeding to step S7 when the adjacent flag is "High" in step S6, or sets the process proceeding to step S12 when the adjacent flag is "Low" (=0).

In the example shown in FIG. 9, it is assumed that the detection signal D3 is input into the pulse detector 51, and the pulse detector 51 detects the rising edge of the first pulse wave in step S3. In such a case, since the adjacent flag is "Low" in step S6, the counting unit 50 sets the process proceeding to step S12.

In step S12, the second counter 502 starts measuring time Tb from the point where the rising edge is detected in step S3. The target counter 503 sets, in association with the second counter 502, the adjacent flag to "High" from the point where the rising edge is detected in step S3, and the process proceeds to step S8.

In step S8, the controller 5 determines whether the scanning of the substrate 100 in a predetermined tracking range by the optical scanning unit 3 is finished. The controller 5 ends the process when the scanning is finished, or sets the process returning to step S1 when the scanning is not yet finished.

In the example shown in FIG. 9, it is assumed that the detection signal D3 is input into the pulse detector 51, and the pulse detector 51 detects the rising edge of the second pulse wave in step S3. In such a case, since the adjacent flag is "High" in step S6, the counting unit 50 sets the process proceeding to step S7.

In step S7, the second counter 502 determines the time Tb from the point where the first rising edge is detected in step S3 to the point where the second rising edge is detected in the next step S3, and resets it. The target counter 503 obtains and holds the time Tb determined by the second counter 502 as a pulse interval Tb of the two pulse waves detected in the two sets of steps S1 to S3, and sets the adjacent flag to "Low".

In step S7, the target counter 503 determines that the optical scanning unit 3 has scanned a plurality of beads 6 adjacent to each other, so as to read out the first pulse width T1 from the storage unit 52 to count the number of beads 66 according to "1+(Tb/T1)". The value obtained from (Tb/T1) is, for example, rounded off to the nearest integer. In the example shown in FIG. 9, when the detection signal D3 is input into the pulse detector 51, the number of beads 66 results in 1+2=3. As described above, when the two pulse waves each having the pulse width Ta less than the first reference value T2 are detected consecutively, the target counter 503 counts the number of beads 66 according to "1+(Tb/T1)". The target counter 503 sets the process proceeding to step S8 after step S7.

When the pulse width Ta is greater than or equal to the first reference value T2 in step S5, the target counter 503 reads out the second reference value T4 from the storage unit 52, and determines in step S9 whether the pulse width Ta held in step S4 is less than the second reference value T4. The target counter 503 sets the process proceeding to step S10 when the pulse width Ta is less than the second reference value T4, or sets the process proceeding to step S11 when the pulse width Ta is greater than or equal to the second reference value T4.

Figure 10:
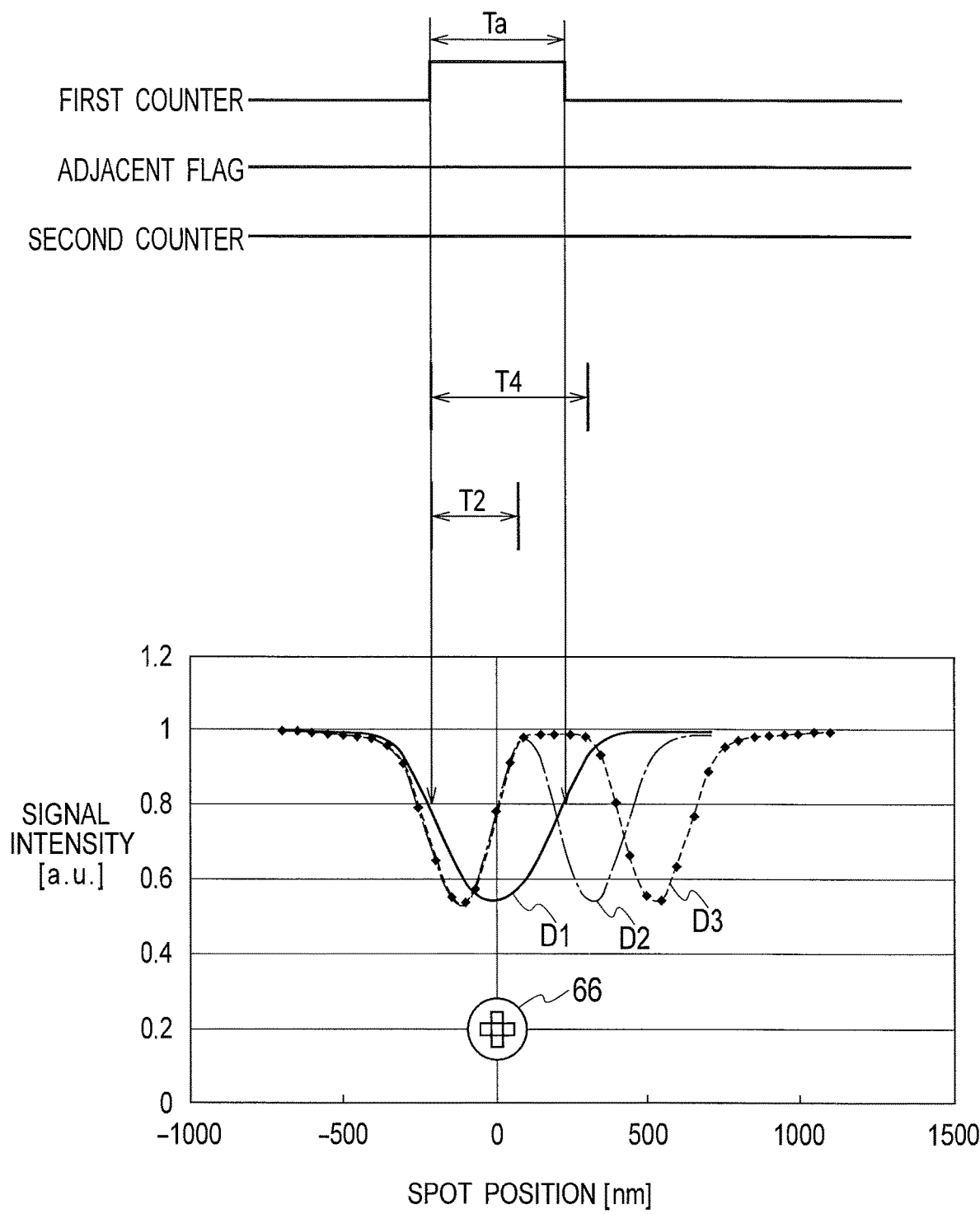
FIG. 10 is a view for describing the operation of the analysis device according to the embodiment.

As shown in the example of FIG. 10, it is assumed that the detection signal D1 is input into the pulse detector 51, and the pulse detector 51 detects the rising edge of the pulse wave in step S3. In such a case, since the pulse width Ta is greater than or equal to the first reference value T2 in step S5, and the pulse width Ta is less than the second reference value T4 in step S9, the counting unit 50 sets the process proceeding to step S10.

In step S10, the target counter 503 determines that the optical scanning unit 3 has scanned one bead 66 isolated from other beads 66 and therefore the count of beads 66 results in one. Thus, the target counter 503 determines that the number of beads 66 counted is one when the pulse wave having the pulse width Ta greater than or equal to the first reference value T2 and less than the second reference value T4 is detected. The target counter 503 then sets the adjacent flag to "Low", and the process proceeds to step S8.

When the pulse width Ta is greater than or equal to the second reference value T4 in step S9, the target counter 503 determines in step S11 that the pulse wave having the pulse width greater than or equal to the second reference value T4 is noise derived from foreign substances or aggregations, so as not to consider the pulse wave when implementing counting processing. The target counter 503 then sets the adjacent flag to "Low", and the process proceeds to step S8.

It is also assumed that the pulse wave having the pulse width Ta less than the first reference value T2 is detected in the first set of steps S1 to S3, and the pulse wave having the pulse width Ta greater than or equal to the first reference value T2 and less than the second reference value T4 is detected in the next set of steps S1 to S3. In such a case, the target counter 503 determines that the pulse wave detected first is noise derived from foreign substances or aggregations, so as not to consider the pulse wave when implementing counting processing.

As described above, when the pulse wave having the pulse width Ta less than the first reference value T2 is detected in the detection signal, the target counter 503 adds the number based on the pulse width Ta and the first pulse width T1 to count up the number of beads 66. When the pulse wave having the pulse width Ta greater than or equal to the first reference value T2 and less than the second reference value T4 is detected in the detection signal, the target counter 503 adds 1 to count up the number of beads 66.

Comparative Example

Figure 11:
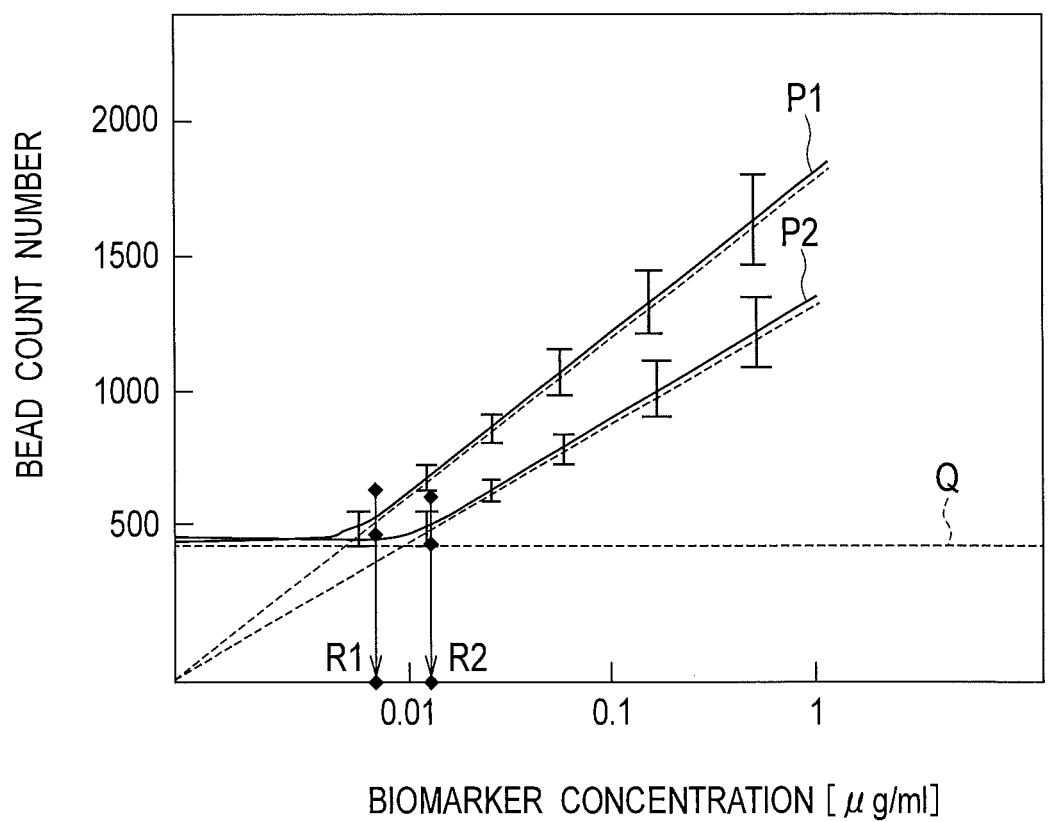
FIG. 11 is a view for comparing characteristics of biomarker concentration and counting results of beads in the analysis device according to the embodiment with those in a conventional device.

A comparative example in which the counted results of beads 66 obtained by the analysis device according to the embodiment are compared with the counted results obtained by a conventional method, is described below with reference to FIG. 11. The transverse axis represents biomarker concentration of analytes, and the vertical axis represents the counted results of beads 66. The counted results obtained by the analysis device according to the embodiment are indicated by the curved line P1, and the counted results obtained by the conventional method are indicated by the curved line P2.

The analysis revealed that the count is entirely smaller in the curved line P2 than the curved line P1 regardless of the biomarker concentration, in which the maximum difference therebetween is several tens of percent. As indicated by the broken lines along the respective curved lines P1 and P2, when the biomarker content is zero, the count would ideally result in zero. In the detection method by use of the antigen-antibody reaction, however, nonspecific adsorption appears on the substrate 100 other than the binding by the antigen-antibody reaction. Even when the biomarker concentration is zero, the beads 66 fixed to the surface of the substrate 100 due to the nonspecific adsorption are thus inevitably counted.

In the respective curved lines P1 and P2, the points of contact (points of intersection) between the lower limits of error and the background noise level Q of the respective curved lines P1 and P2 are respectively denoted by the limits of detection R1 and R2. The limit of detection R1 in the analysis device according to the embodiment is improved compared with the limit of detection R2 in the conventional method, and it is apparent that the sensitivity of the biomarker detection is improved. Accordingly, the analysis device according to the embodiment can improve the sensitivity for detecting diseases.

The analysis device according to the embodiment varies the number to be added depending on the pulse width of the detection signal to count up the beads 66 when a plurality of beads 66 adjacent to each other are fixed onto the substrate 100. Therefore, the analysis device according to the embodiment can count the beads 66 with high accuracy to improve the quantitative analysis of analytes even when irregular pulse waves are detected in the detection signal because of arrangement of the beads 66.

Further, since the first reference value T2 and the second reference value T4 are determined in view of the jitter value of the detection signal, the analysis device according to the embodiment can count the beads 66 with higher accuracy, so as to reduce the influence of jitter when classifying the pulse width Ta.

Other Embodiments

While the present invention has been described above by reference to the embodiment, the present invention is not intended to be limited to the descriptions and drawings which form part of the disclosure. Various alternative embodiments, examples, and practical applications will be apparent to those skilled in the art from this disclosure.

For example, in the embodiment described above, the combination of the biomaterials as analytes and specific biomaterials specifically binding to the analytes is not limited to the combination of the antigens 62 and the antibodies 61 and antibodies 65 fixed to the beads 66. Examples of specifically-binding combinations include a combination of a ligand and an acceptor (such as enzymatic proteins, lectins, and hormones), and a combination of nucleic acids having complementary base sequences to each other.

Alternatively, a well formed of, for example, silicone rubber may be provided on the surface of the substrate 100, and the reaction between the target antibodies 61, antigens 62 and beads 66 and the removal of materials not reacted by washing may be implemented within the well, so as to exclude the steps of, for example, spin washing and drying to simplify the process. Further, a plurality of wells may be provided in the same radius within the allowable area of the substrate 100, so as to measure a plurality of specimens simultaneously.

The present invention includes a program for executing, by a computer, the functions of a notifying device according to the embodiment described above. The program may be read out from a storage medium and input into the computer, or may be transmitted via an electrical communication circuit and input into the computer.

The present invention, of course, includes other embodiments not described in this description, such as embodiments including the above-described configurations mutually applied. Therefore, the scope of the present invention is defined only by the appropriate features according to the claims in view of the explanations made above.

What is claimed is:

1. An analysis method comprising:
   irradiating laser light onto a surface of a substrate to which particles are fixed, and generating a detection signal based on reflected laser light reflected from the substrate;
   detecting a pulse wave and a pulse width of the pulse wave included in the detection signal; and
   counting the particles based on a pulse interval between two pulse waves each having a pulse width less than a first reference value when the two pulse waves are consecutively detected,
   wherein the first reference value is a sum of a first pulse width and a predetermined value, the first pulse width being a pulse width detected when adjacent ones of the particles are scanned by irradiating the laser light onto the surface, and the predetermined value being 100% to 130% of a jitter value included in the detection signal.

2. The analysis method according to claim 1, wherein, when the two pulse waves each having the pulse width less than the first reference value are consecutively detected, the counting of the particles includes counting the particles based on a number obtained by dividing the pulse interval between the two pulse waves by the first pulse width.

3. The analysis method according to claim 1, wherein the counting of the particles includes determining that a particle count is one when a pulse wave having a pulse width greater than or equal to the first reference value and less than a second reference value is detected, wherein the second reference value is a sum of a second pulse width and the predetermined value included in the detection signal, the second pulse width being a pulse width detected when a particle isolated from other ones of the particles is scanned by irradiating the laser light onto the surface.

4. The analysis method according to claim 3, wherein, when the pulse wave having the pulse width less than the first reference value is detected, and subsequently the pulse wave having the pulse width greater than or equal to the first reference value and less than the second reference value is detected, the counting the particles does not include counting the pulse wave having the pulse width less than the first reference value detected first.

5. The analysis method according to claim 3, wherein, when a pulse wave having a pulse width greater than or equal to the second reference value is detected, the counting the particles does not include counting the pulse wave having the pulse width greater than or equal to the second reference value.

* * * * *